United States Patent
Tran et al.

(10) Patent No.: US 7,867,435 B2
(45) Date of Patent: Jan. 11, 2011

(54) MANUFACTURE OF INFLATABLE MEMBER FOR BIFURCATION CATHETER ASSEMBLY

(75) Inventors: The Thomas Trin Tran, Coon Rapids, MN (US); Richard A. Noddin, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/052,799

(22) Filed: Mar. 21, 2008

(65) Prior Publication Data

US 2009/0236773 A1   Sep. 24, 2009

(51) Int. Cl.
*B29C 67/00* (2006.01)

(52) U.S. Cl. .................. 264/532; 264/520; 264/521; 264/531; 425/529; 425/577

(58) Field of Classification Search ............ 264/532, 264/520, 521, 531; 425/529, 577
See application file for complete search history.

(56) References Cited

U.S. PATENT DOCUMENTS

| | | | |
|---|---|---|---|
| 3,764,644 A * | 10/1973 | Robinson | 264/531 |
| 4,432,719 A * | 2/1984 | Hafele | 425/526 |
| 5,163,989 A * | 11/1992 | Campbell et al. | 65/110 |
| 6,146,356 A | 11/2000 | Wang et al. | |
| 6,168,748 B1 * | 1/2001 | Wang et al. | 264/520 |
| 2002/0150703 A1 * | 10/2002 | Collette et al. | 428/34.1 |
| 2005/0011607 A1 * | 1/2005 | Hensley et al. | 156/245 |
| 2005/0015108 A1 | 1/2005 | Williams et al. | |
| 2005/0102019 A1 | 5/2005 | Yadin | |

FOREIGN PATENT DOCUMENTS

WO    WO 2005041810 A2 *   5/2005

* cited by examiner

*Primary Examiner*—Philip C Tucker
*Assistant Examiner*—Amjad Abraham
(74) *Attorney, Agent, or Firm*—Seager, Tufte & Wickhem, LLC (57) ABSTRACT

A catheter inflatable member forming mold can include first and second frames that mate to define a mold cavity, the mold cavity defining a main cavity portion and a bulge cavity portion, the mold cavity being sized to receive an elongated tube member therein. The mold can also include a pin member with a head portion positioned in the mold cavity, the pin member extending into the mold cavity, the head portion of the pin member being moveable in a first direction to contact and move the tube member towards the bulge cavity portion of the mold cavity during molding.

8 Claims, 13 Drawing Sheets

MANUFACTURE OF INFLATABLE MEMBER FOR BIFURCATION CATHETER ASSEMBLY

TECHNICAL FIELD

This disclosure relates to catheter systems and methods for treating vessel bifurcations.

BACKGROUND

Catheters are used with stents and balloon inflatable structures to treat strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular body organ for treating conditions such as, for example, occlusions, stenoses, aneurysms, dissection, or weakened, diseased, or abnormally dilated vessel or vessel wall, by expanding the vessel or by reinforcing the vessel wall. Once delivered, the stents can be expanded using one or more inflatable members such as balloons. Stents can improve angioplasty results by preventing elastic recoil and by remodeling of the vessel wall and treating dissections in blood vessel walls caused by balloon angioplasty of coronary arteries. Stents can also be used as a drug delivery medium for treatment of damaged portions of a vessel.

While conventional stent technology is relatively well developed, stent technologies related to treatment of the region of a vessel bifurcation are still being developed.

SUMMARY

The present disclosure relates generally to catheter assemblies for treatment of bifurcated lumens in a patient, such as vessel bifurcations.

In one arrangement, a mold includes a mold cavity sized to form an inflatable member of a catheter assembly. An elongated tube member is heated and expanded within the mold cavity to form the inflatable member. A pin member extends into the mold cavity to contact the tube member during molding. The pin member influences the molding of the tube member, which includes a main inflatable portion and a bulge portion.

There is no requirement that an arrangement or method include all features characterized herein to obtain some advantage according to this disclosure.

DETAILED DESCRIPTION

I. Overview

This disclosure relates to bifurcation treatment systems, catheter assemblies, and related methods of treating bifurcations in a patient's body. The term "bifurcation" means a division location from one unit into two or more units. Generally, two types of bifurcations of a body organ include: 1) a main tubular member defining a main lumen and a branch tubular member defining a branch lumen that extends or branches off from the main tubular member, wherein the main and branch lumens are in fluid communication with each other; and 2) a primary or main member defining a primary or main lumen (also referred to as a parent lumen) that splits into first and second branch members defining first and second branch lumens. The term "lumen" means the cavity or bore of a tubular structure such as a tubular organ (e.g., a blood vessel).

Example applications of the principles disclosed herein include cardiac, coronary, renal, peripheral vascular, gastrointestinal, pulmonary, urinary, and neurovascular systems. Bifurcated vessels in such systems can become partially or fully blocked over time, which is referred to as stenosis of the artery. There are various procedures to treat the stenosis of a vessel, including angioplasty and/or the placement of a stent at the point of stenosis to reopen the vessel. Restenosis of the bifurcated vessel can occur over time. It is desirable to minimize the effects of restenosis.

The catheter assemblies, systems and methods disclosed herein can be used for locating a branch vessel of the vessel bifurcation and for treatment of stenoses of such vessels.

II. The Example Precursors and Inflatable Members Illustrated in FIGS. 1-5

Figure 1:
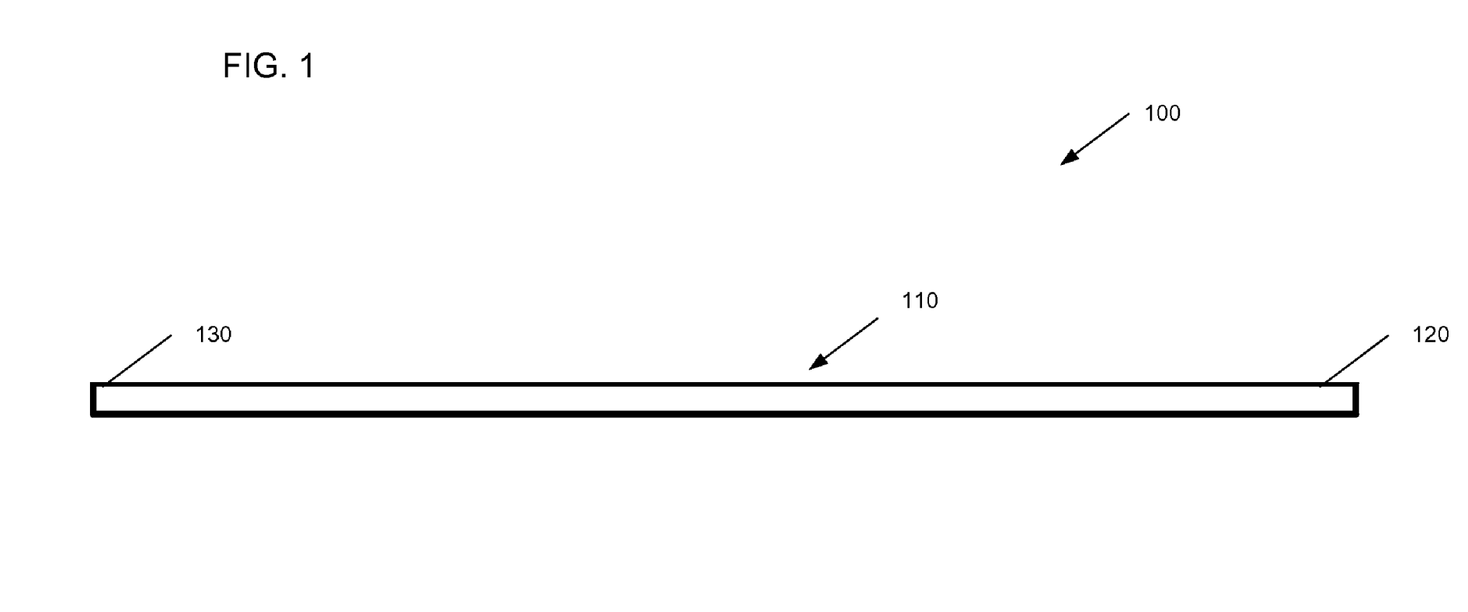
FIG. 1 is a schematic representation of an example precursor used to form an inflatable member for use with a system to treat a vessel bifurcation.

Referring now to FIG. 1, an example precursor 100 (sometimes referred to herein as a "member") is shown. The precursor 100 is an elongated tube with a midportion 110, and first and second end portions 120, 130. In some examples, the precursor 100 is formed by extruding a tube of polymeric material, although other methods of formation can be used.

In example arrangements, the precursor 100 is used to form an inflatable member (sometimes referred to as a balloon) of a bifurcated catheter assembly. For example, the precursor 100 can be geometrically modified to create specialized zones that possess differences in cross-sectional dimension and polymer orientations. This can result in an inflatable member having enhanced wall thicknesses and strength characteristics, as described further below.

Figure 2:
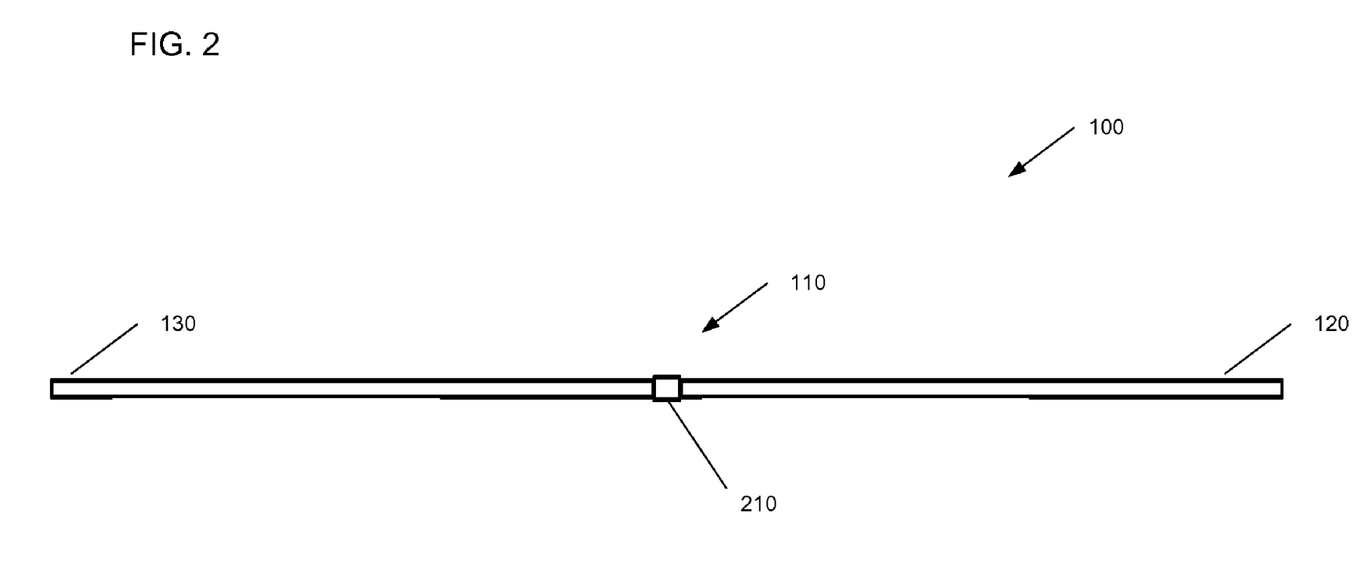
FIG. 2 is another schematic representation of the example precursor of FIG. 1.

Referring now to FIG. 2, the precursor 100 is shown with a nugget 210 formed at the midportion 110 of the precursor 100. In example arrangements, the nugget 210 is used to form an inflation portion of an inflatable member, including a bulge portion. The end portions 120, 130 are used to form the waists of the inflatable member.

The nugget 210 can be formed using various methods. In one arrangement, the nugget 210 is formed by pulling the end portions 120, 130 of the precursor 100 through one or more heated dies. In addition, air can thereupon be drawn through the precursor 100. This air drawn technique causes the end portions 120, 130 of the precursor to be stretched to a smaller diameter than the midportion 110. The larger diameter midportion 110 forms the nugget 210, while the smaller diameter portions form the end portions 120, 130.

For example, in one arrangement, the precursor 100 is a 4 mm diameter tube having an approximate length of 305 mm. The precursor 100 is stretched through heated dies (e.g., 115 degrees C.) to reduce the diameter of the end portions 120, 130 to 3 mm, while maintaining the midportion 110 at 4 mm to form the nugget 210. In some embodiments, the nugget 210 is air-cooled during the stretching process to maintain the nugget 210 at a greater thickness. In addition to changes in the diameter of the precursor 100, the thickness of the walls of the precursor 100 are varied. For example, in the arrangement shown, the thickness of the wall of the nugget 210 and end portions 120, 130 is approximately 0.622 mm.

Other sizes for the precursor 100 are possible. For example, precursors having diameters of 2.5 mm or 3.0 mm and wall thicknesses of 0.389 mm and 0.445 mm can be used.

Figure 3:
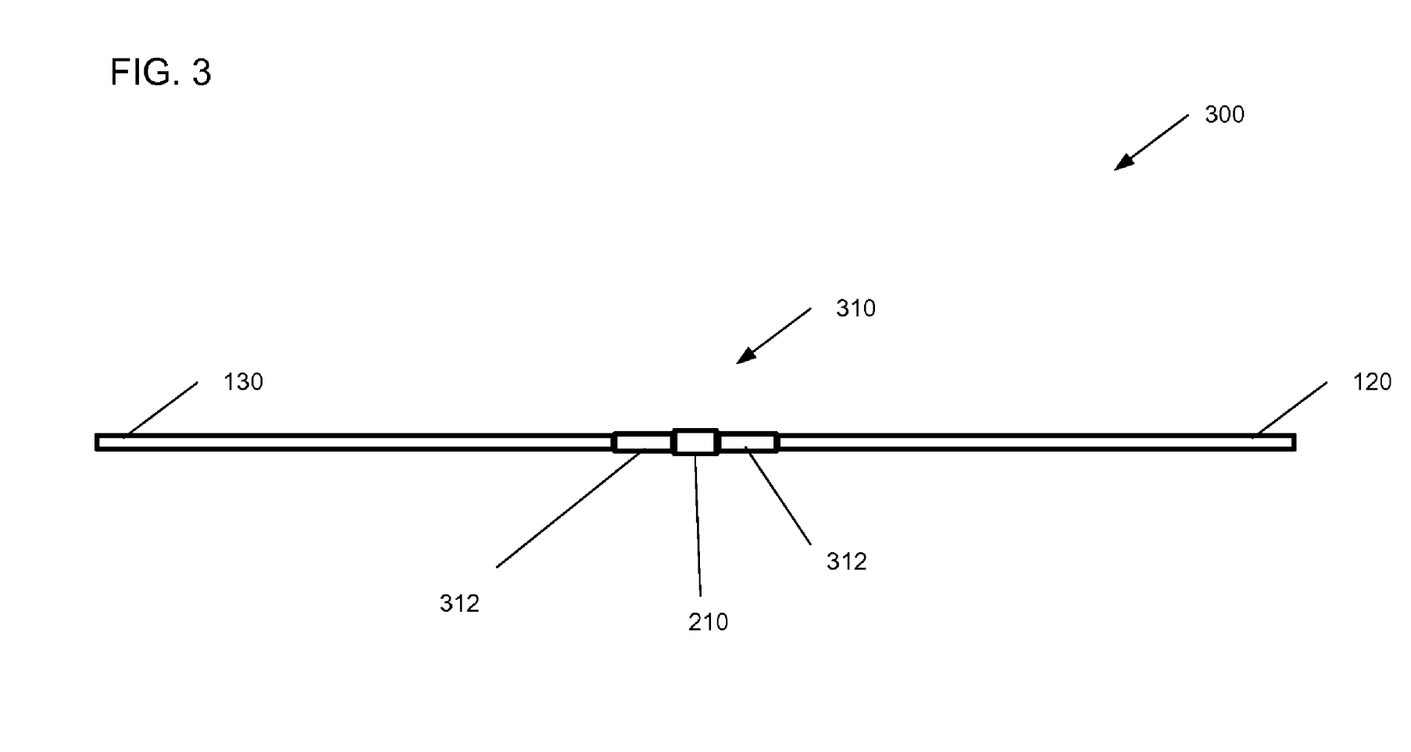
FIG. 3 is a schematic representation of another example precursor used to form an inflatable member for use with a system to treat a vessel bifurcation.

Referring now to FIG. 3, another example precursor 300 is shown. The precursor 300 is similar to that of the precursor 100, except that the precursor 300 includes stepped portions 312 surrounding the nugget 210. In one example, the stepped portions 312 are formed by the stretching of the precursor 300 through a stepped heated die, although other formation methods can be used.

Precursors of other configurations can be used. For example, in other arrangements, the nugget and/or stepped portions can be formed offset from the midportion. In yet other arrangements, multiple nuggets and/or stepped portions can be formed in the precursor.

Other methods can be used to form nuggets 210 and stepped portions 312. For example, using air pressure to stretch the precursor is another way for form nugget 210 and stepped portion 312.

Figure 4:
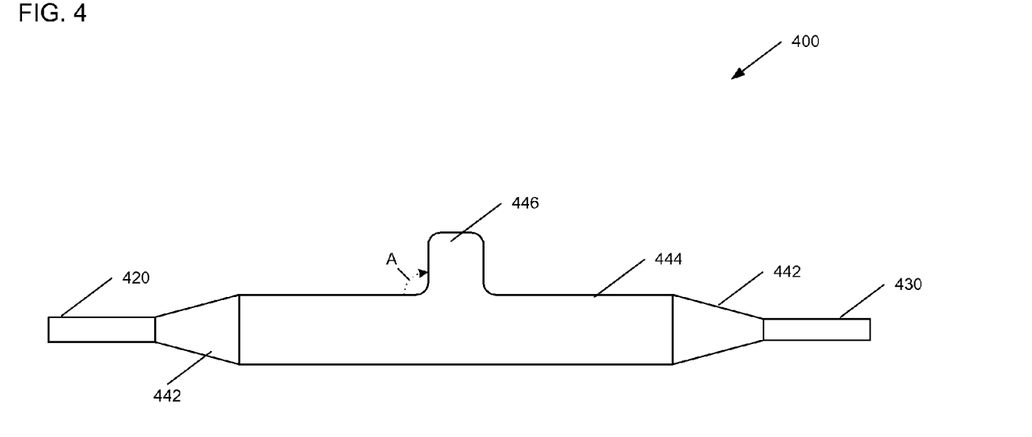
FIG. 4 is a side schematic representation of an example inflatable member formed from the precursor of FIG. 3.
Figure 5:
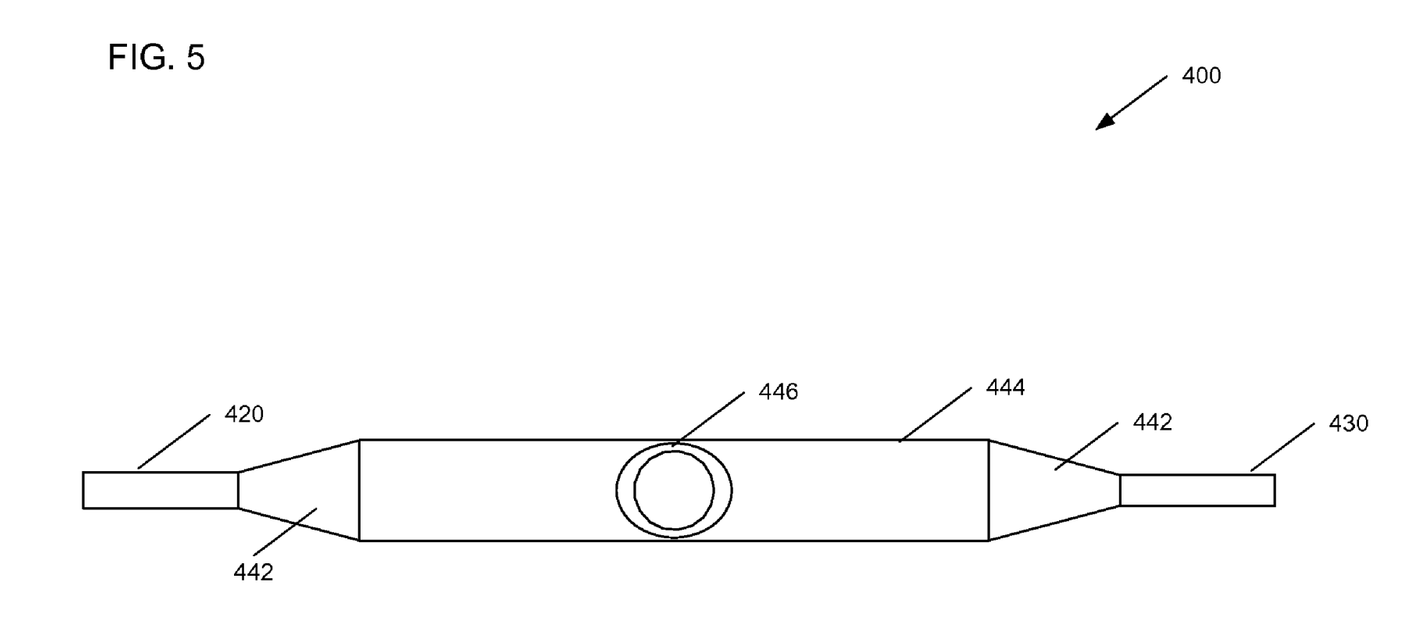
FIG. 5 is a top schematic representation of the example inflatable member of FIG. 4.

Referring now to FIGS. 4 and 5, an example inflatable member 400 is shown in an inflated state. The inflatable member 400 includes a main inflation portion 444 having a bulge 446 extending radially therefrom. In example arrangements, the bulge 446 extends at an angle A with respect to the main inflation portion 444. The angle A is between approximately 110 and 140 degrees, more preferably 125 or 150 degrees. The inflatable member 400 also includes tapered portions 442 that extend to waist portions 420, 430.

In the arrangement shown, the inflatable member 400 is formed from the precursor 300 shown in FIG. 3. Specifically, the main inflation portion 444 and the bulge 446 are formed by the nugget 210, and the tapered portions 442 are formed by the stepped portions 312. The waist portions 420, 430 are formed by the end portions 120, 130 of the precursor 300. The inflatable member 400 can be formed from the precursor 300 using one or more of the systems and methods described below.

In example arrangements, the inflatable member 400 shown in FIGS. 4 and 5 is used in conjunction with a bifurcated catheter assembly (not shown). The bifurcated catheter assembly can include a main catheter branch and a side catheter branch. The inflatable member 400 is coupled to the main catheter branch, and a stent can be positioned to surround the inflatable member.

During deployment, the inflatable member 400 is inflated so that the main inflation portion 444 expands the stent in the main portion of a blood vessel, and the bulge 446 expands the lateral branch opening of the stent through an ostium into a branch portion of the vessel. Further details of such a bifurcated catheter assembly are described in U.S. patent application Ser. No. 10/834,066 filed on Apr. 29, 2004, and U.S. patent application Ser. No. 10/985,005 filed on Nov. 10, 2004, which are hereby incorporated by reference.

III. The Examples in FIGS. 6-10

Figure 6:
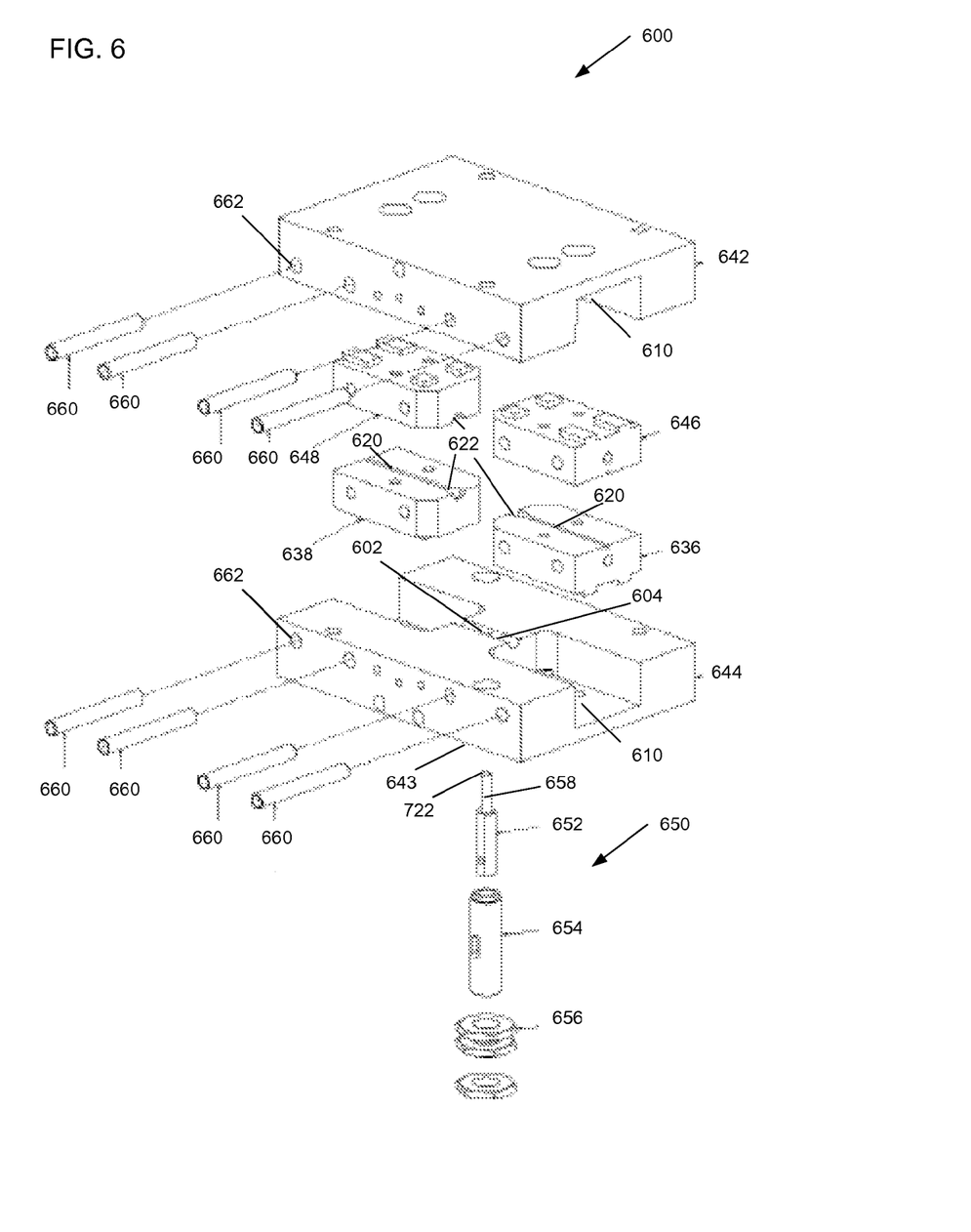
FIG. 6 is a perspective schematic representation of an example molding system used to form an inflatable member for use with a system to treat a vessel bifurcation.

Referring now to FIG. 6, an example molding system 600 is shown for forming an inflatable member, such as inflatable member 400, from a precursor, such as precursor 300. Generally, the precursor 300 is placed into the system 600. Heat is applied by the system 600, and the precursor 300 is expanded to form the inflatable member 400.

As shown in FIG. 6, the system 600 includes top and bottom frames 642, 644. Each of the frames 642, 644 defines a mold cavity portion 604. A portion of the mold cavity 604 of the top frame 642 also includes a bulge portion 710 (see FIGS. 7-10). The mold cavity portion 604 of the bottom frame 644 also includes an aperture 602 that extends from a bottom side 643 of the bottom frame 644 to the mold cavity portion 604. The frames 642, 644 include a plurality of apertures 662 into which cooling tubes 660 can be placed to cool frames 642, 644 as needed.

The frames 642, 644 also form side cavities 610 that receive frame inserts 636, 638, 646, 648 therein. The frame inserts 636, 638, 646, 648 each form cavity portions 620 with enlarged portions 622. When assembled, the cavity portions 604, 620 of frames 642, 644 and frame inserts 636, 638, 646, 648 together define a cavity 665 (see FIGS. 7 and 8) in which a precursor is placed to form an inflatable member, such as inflatable member 400 shown in FIGS. 4 and 5.

To form the inflatable member 400, the precursor 300 is placed in the cavity 665 of the system 600 so that the nugget 210 and stepped portions 312 are positioned in the cavity portion 604 of the frames 642, 644. The end portions 120, 130 extend through the cavity portions 620 of the frame inserts 636, 638, 646, 648. In this position, heat is applied to the system 600 and the precursor 300 is inflated to form the inflatable member 400, as described further below.

For example, in one arrangement, the cavity portion 604 of the frames 642, 644 forms the main inflation portion 444 and bulge 446 of the inflatable member 400. The enlarged portions 622 of the frame inserts 636, 638, 646, 648 form the tapered portions 442 of the inflatable member 400, and the remainder of the cavity portions 620 form the waists 420, 430 of the inflatable member 400.

The system 600 also includes an actuator member 650 with a cylinder 654 and a pin member 652 having a head portion 658. The pin member 652 is positioned to extend through the aperture 602 in the bottom frame 644 perpendicular to a longitudinal axis of the precursor 300. Fasteners 656 are used to connect the cylinder 654 to the bottom side 643 of the bottom frame 644. The pin member 652 moves longitudinally within the cylinder 654 so that the head portion 658 extends partially into the mold cavity portion 604, as described further below.

Figure 7:
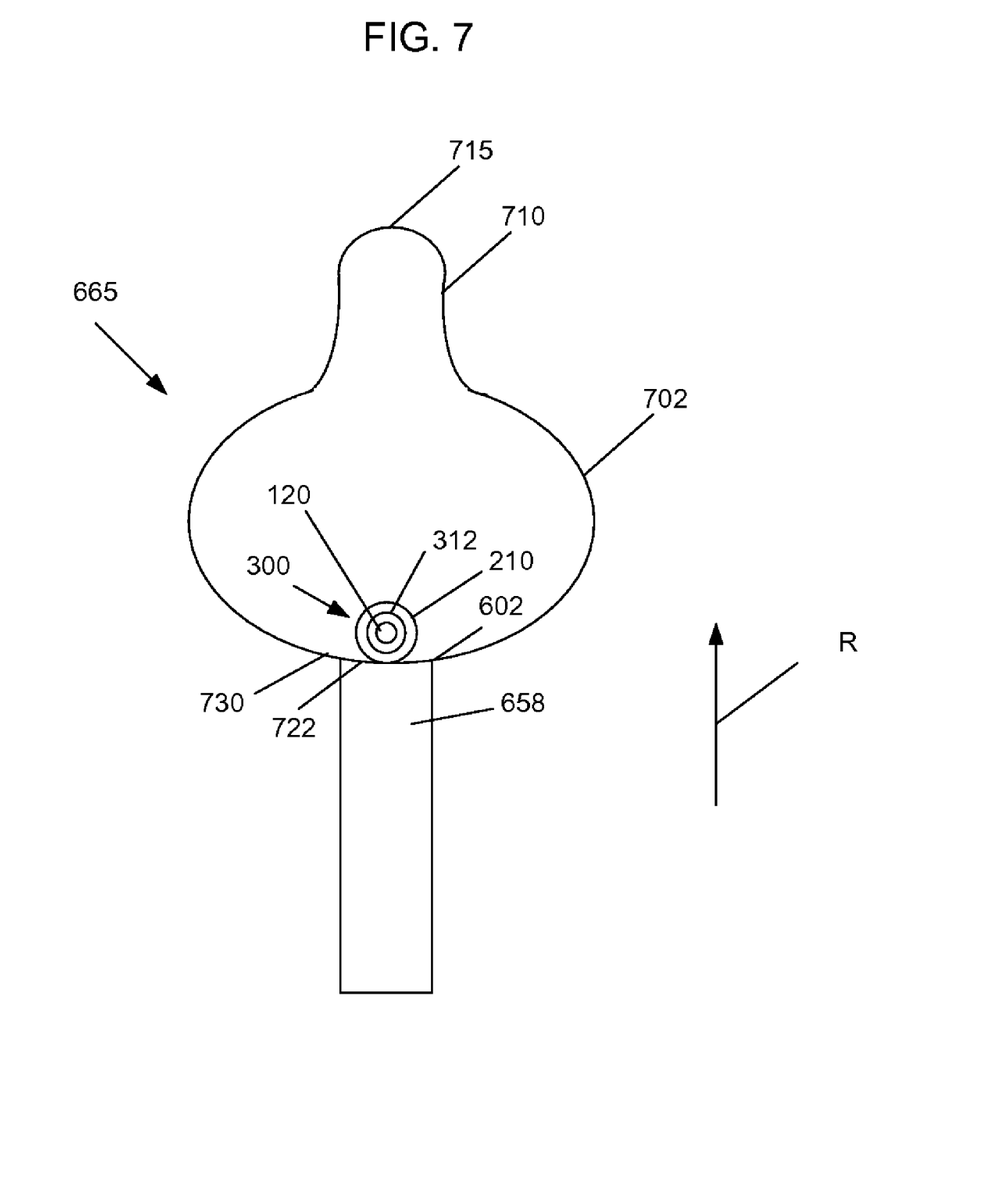
FIG. 7 is a schematic view of a portion of the main cavity of the example molding system of FIG. 6.

Referring now to FIG. 7, a schematic view of a portion of the cavity 665 formed by the system 600 is shown. Generally, the cavity 665 includes a main cavity portion 702 and a bulge portion 710 formed by cavity portions 604 of the mating frames 642, 644. The main cavity portion 702 forms the main inflation portion 444 of the inflatable member 400, and the bulge portion 710 forms the bulge 446 of the inflatable member 400.

The head portion 658 of the actuator member 650 (see FIG. 6) extends through the aperture 602 in a base 730 of the main cavity portion 702. An end surface 722 of the head portion 658 coincides with and forms a portion of the base 730 upon which the nugget 210 of the precursor 300 rests prior to molding. Fasteners 656 (see FIG. 6) can be adjusted to change the height of the end surface 722 to coincide with the base 730.

To mold the precursor 300 into the inflatable member 400, the system 600 including the main cavity portion 702 is heated. In example embodiments, the system 600 is heated to between approximately 90 and 150 degrees Celsius, more preferably between approximately 95 and 130 degrees Celsius, and even more preferably 100 degrees Celsius. The amount of heat applied can vary depending on the materials of the molding system and the precursor.

In addition to heating, a fluid (liquid or gas) is introduced into the precursor 300 to inflate the precursor. As the precursor 300 is heated and inflated, the precursor 300 is molded into the desired shape. The nugget 210 conforms to the shape of the main cavity portion 702 and the bulge portion 710 to form the main inflation portion 444 and the bulge 446.

As the precursor 300 is heated and expanded, the thickness of the wall of the precursor 300 varies. For example, as the nugget 210 is heated and expanded into the bulge portion 710 of the cavity 665 to form the bulge 446, the thickness of the wall of the nugget 210 of the precursor 300 thins, particularly at an outer surface 715 of the bulge portion 710.

It is desirable to influence this thinning such that the walls of the resulting inflatable member 400 have sufficient thickness to withstand the pressures associated with expansion of the inflatable member 400, while still allowing the inflatable member 400 to be folded prior to expansion. It is also desirable to influence the wall thickness to control inflation dimensions and sequences of inflation of the various parts of the inflatable member 400.

For example, in some arrangements it is desirable to have the inflation portion 444 expand at least partially before the bulge 446 for proper deployment. By varying the amount of heat applied to different sections of the nugget 210, the resulting wall thickness in the inflatable member 400 can be manipulated. To accomplish this, the position of the precursor 300 within the cavity 665 is manipulated during heating and expansion. This changes the characteristics of the resulting inflatable member 400 during prior to and during expansion.

As shown in FIG. 7, the precursor 300 is positioned within the cavity 665 to rest on the end surface 722 of the head portion 658 of the actuator member 650. During molding, the head portion 658 is moved in a direction R so that the nugget 210 is moved closer to the bulge portion 710 of the mold cavity 665.

Figure 8:
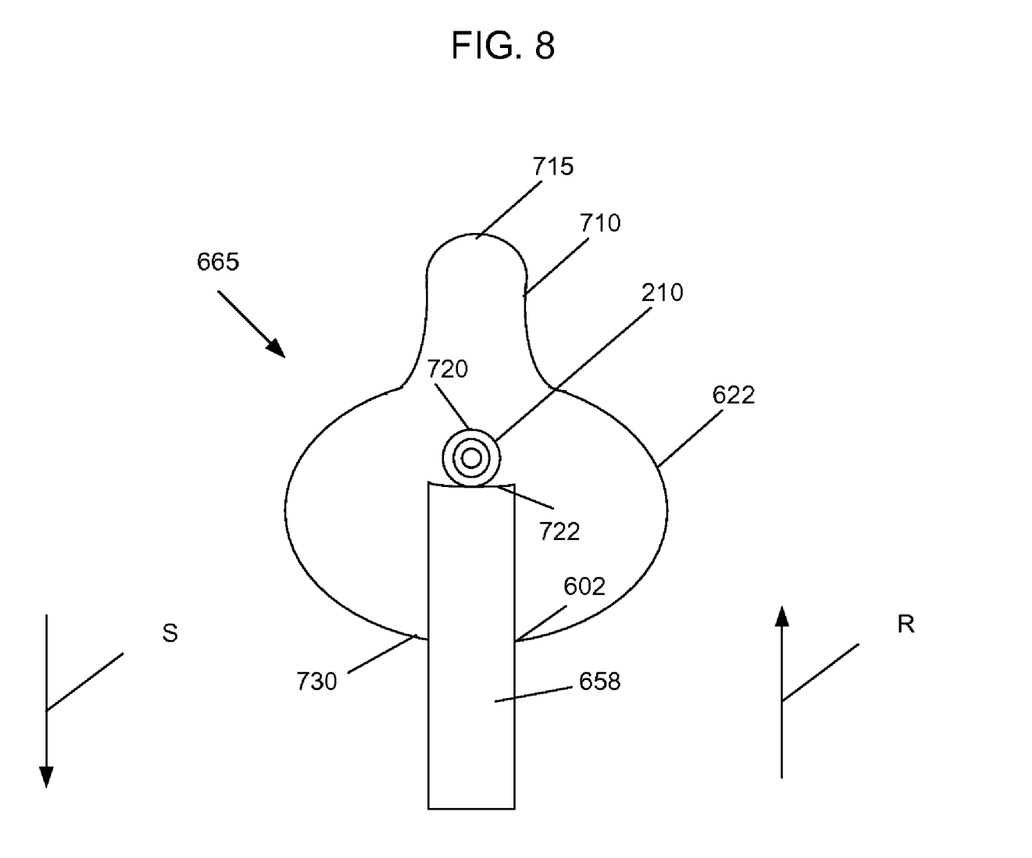
FIG. 8 is another schematic view of the portion of the main cavity of FIG. 7.
Figure 9:
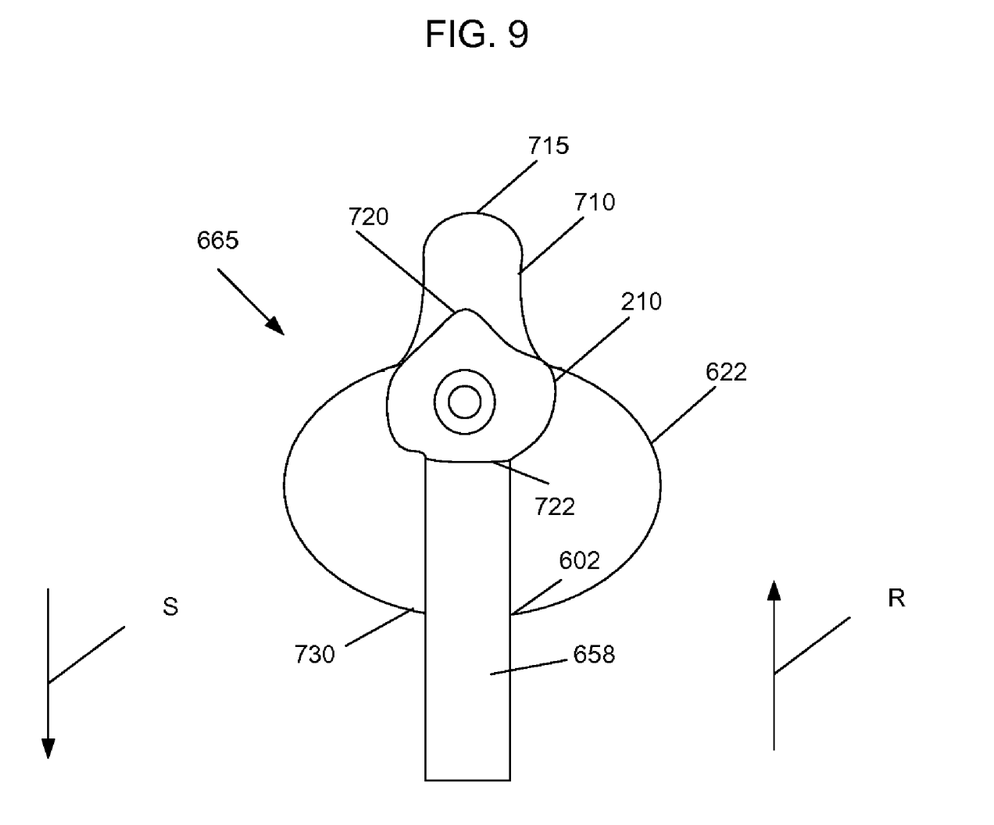
FIG. 9 is another schematic view of the portion of the main cavity of FIG. 7 with a precursor in a semi-inflated configuration during molding.
Figure 10:
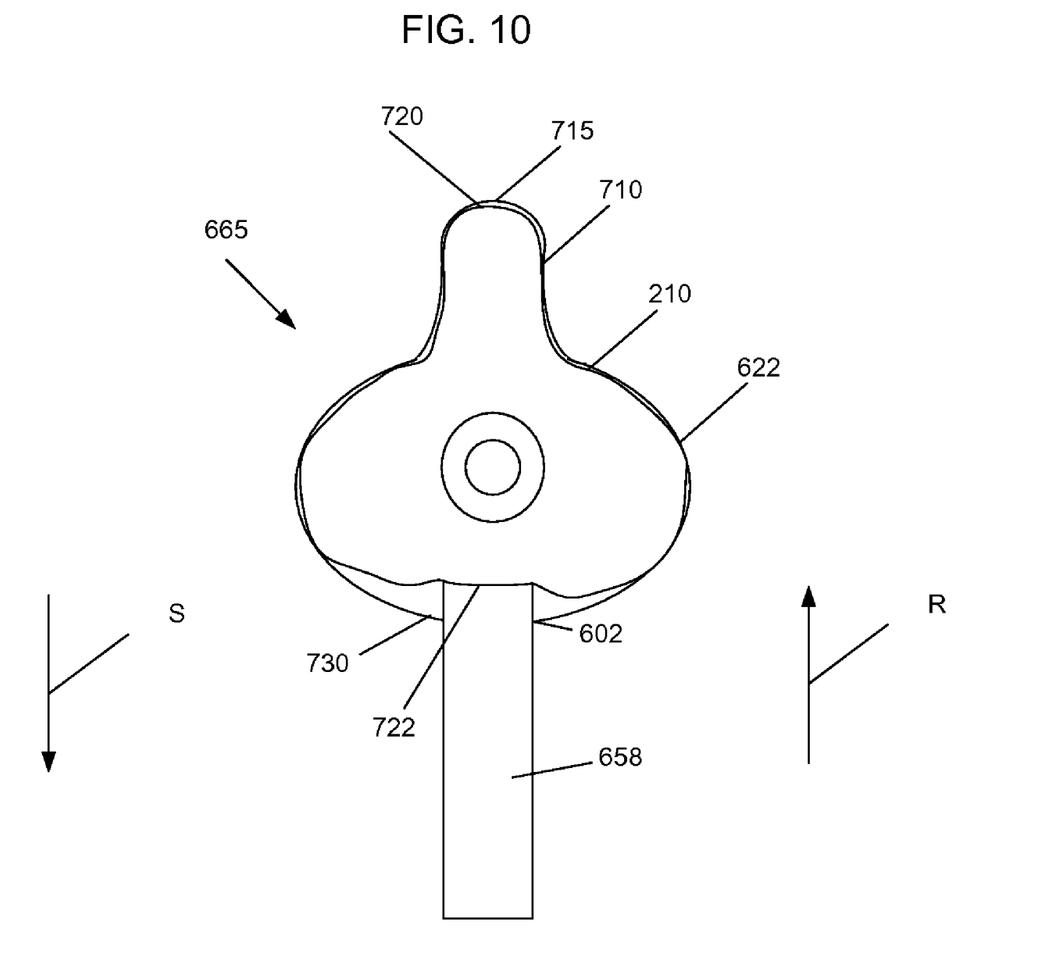
FIG. 10 is another schematic view of the portion of the main cavity of FIG. 7 with a precursor in a semi-inflated configuration during molding.

For example, referring now to FIG. 8, the head portion 658 is moved in the direction R through the aperture 602. The nugget 210 of the precursor 300 is carried on the end surface 722 of the head portion 658 towards the bulge portion 710 of the mold cavity 665. As the mold cavity 665 is heated and the precursor 300 is inflated, the precursor 300 expands into and fills the cavity 665, including the bulge portion 710.

Since the nugget 210 is closer to the bulge portion 710 of the cavity 665, the nugget 210 expands into the bulge portion 710 sooner than if the precursor 300 is positioned at the base 730 of the cavity 665. In this manner, an upper surface 720 of the nugget 210 expands into the bulge 710 more quickly, thereby maintaining a greater wall thickness during molding.

As the inflated precursor 300 fills the bulge portion 710, the precursor 300 exerts pressure against the head portion 658 in a direction S opposite to that of the direction R. See FIG. 9. At some point during inflation, the pressure is greater than the pressure exerted on the head portion 658, so that the precursor 300 forces the head portion 658 in the direction S as the precursor 300 is further inflated and fills the cavity 665. See FIG. 10. Upon full inflation, the precursor 300 fills the entirety of the cavity 665 (including the bulge portion 710), and the head portion 658 is forced in the direction S until the end surface 722 is again flush with the base 730 of the cavity 665.

In example embodiments, gas is introduced into the cylinder 654 to move the pin member 652 and associated head portion 658 in the direction R to a desired height relative to the base 730. In one example, a regulated supply of $N_2$ gas is delivered to the cylinder 654 to move the pin member 652, although other gases or liquids can also be used.

The pressure of the gas is regulated to control the pressure at which the pin member 652 is moved in the direction R. In one example, the gas is supplied at a pressure of between approximately 50 and 150 psi, more preferably between approximately 80 and 120 psi, and even more preferably at a pressure of approximately 100 psi. The desired pressure can vary depending, for example, on the characteristics of the mold and precursor.

In example embodiments, the upper surface 720 of nugget 210 maintains a thickness of approximately 0.001 mm, although other thicknesses are possible. In addition, the bulge 446 of the balloon exhibits enhanced expansion characteristics. For example, it is desirable to have the bulge 446 expand a specified distance from the main inflation portions 444, such as approximately 1 to 3 mm, more preferably approximately 2 mm or at least 1.5 mm.

In addition to the position of the precursor 300 within the cavity 665, the heat applied during molding can be varied to influence the wall thickness of the resulting inflatable member 400. For example, in one arrangement, additional heat is applied through the head portion 658 so that the section of the precursor 300 that is in contact with the end surface 722 of the head portion 658 is heated more quickly than the other sections of the precursor 300.

In one example, when the system 600 is closed, the precursor 300 is held at the elevated position for approximately between 1 and 20 seconds, more preferably between approximately 3 and 10 seconds, and even more preferably 5 seconds. The entire mold cycle takes approximately between 30 and 75 seconds. The heat is applied continuously to the mold during the mold cycle, or can be varied during the mold cycle.

In example arrangements, the geometry of the end surface 722 of the head portion 658 can be modified to change the influence of the end surface 722 on the nugget 210. For example, the end surface 722 can be contoured so that a greater surface area of the end surface 722 contacts the nugget 210 so that more heat is transferred from the end surface 722 to the nugget 210. Other configurations are possible.

Various materials can be used to form the head portion 658. In examples, the head portion is made of stainless steel, Polyetheretherketones (PEEK), or brass. The material can be selected based on the desired thermal conductivity characteristics. In other examples, the head portion 658 is a composite material selected based on desired thermal characteristics.

Further, heating of the various components of the system 600 can also be manipulated. For example, the frame inserts 636, 638, 646, 648 can be made of a first material, such as copper. The frames 642, 644 can be made of a second material, such as stainless steel. The differences in the materials results in a difference in the speed at which the materials are heated and cooled. For example, the copper of the frame inserts 636, 638, 646, 648 can cool more quickly than the stainless steel of the frames 642, 644 to thereby influence the expansion characteristics of the resulting inflatable member 400. In addition, cooling fluids (liquids or gases) can be introduced into one or more of the cooling tubes 660 to cool frames 642, 644, as needed, to cool the frames 642, 644 during molding.

By controlling the position of the precursor 300 within the cavity 665, as well as the heating of the various sections of the cavity 665, the wall thickness and expansion characteristics of the resulting inflatable member 400 can thereby be influenced. This influence can lead to enhanced folding of the inflatable member 400 prior to deployment, as well as enhanced deployability once the inflatable member 400 is in position.

IV. The Examples in FIGS. 11-13

Figure 11:
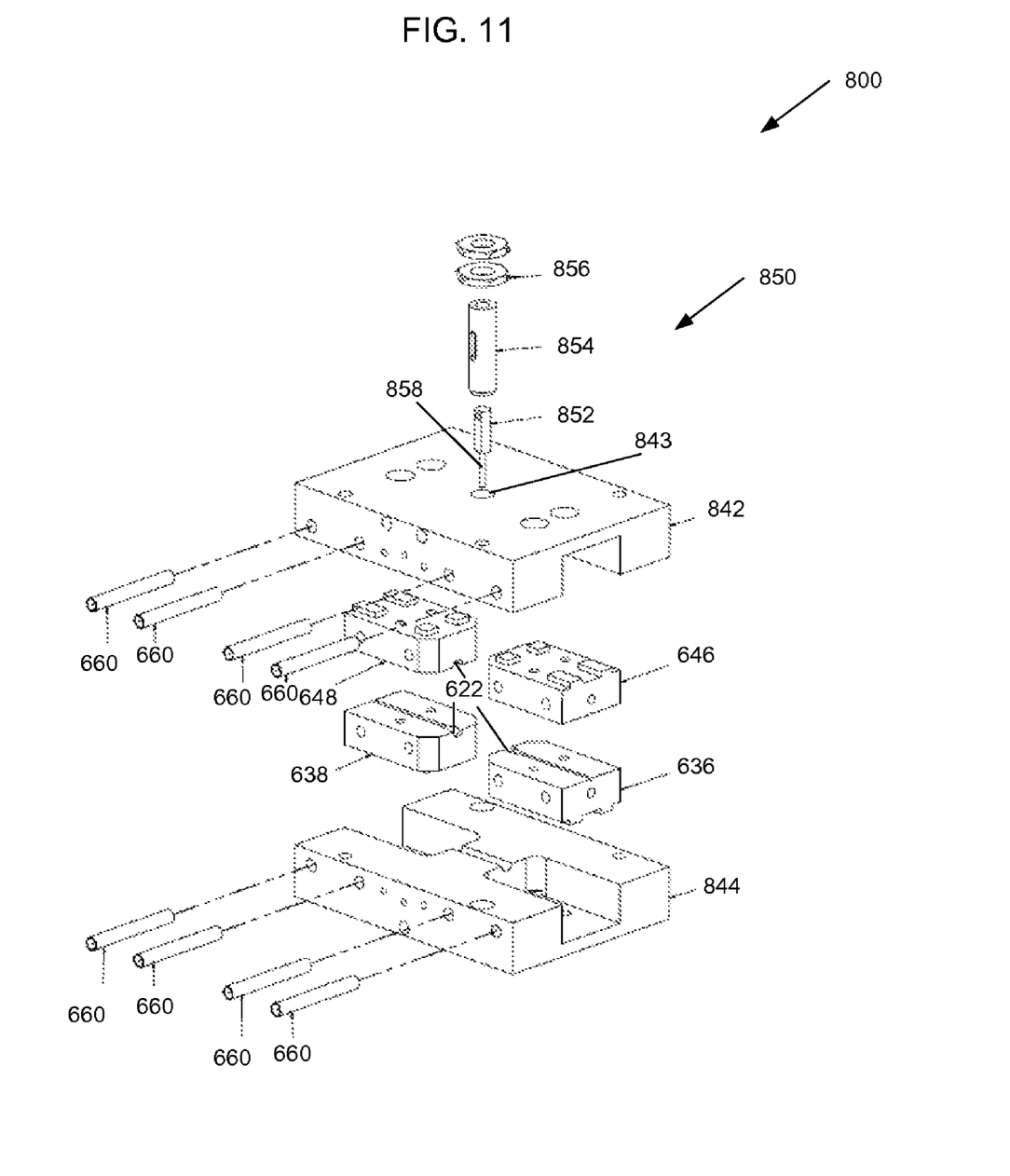
FIG. 11 is a perspective schematic representation of another example molding system used to form an inflatable member for use with a system to treat a vessel bifurcation.

Referring now to FIG. 11, another example mold system 800 is shown. The system 800 is similar to that of the system 600, except that an actuator member 850 with a cylinder 854 and a pin member 852 having a head portion 858 is positioned to extend through an aperture 843 in the top frame 842. Fasteners 856 are used to connect the cylinder 854 to the top frame 644. The pin member 852 moves longitudinally within the cylinder 854 so that the head portion 858 extends partially into mold cavity portion 604.

Figure 12:
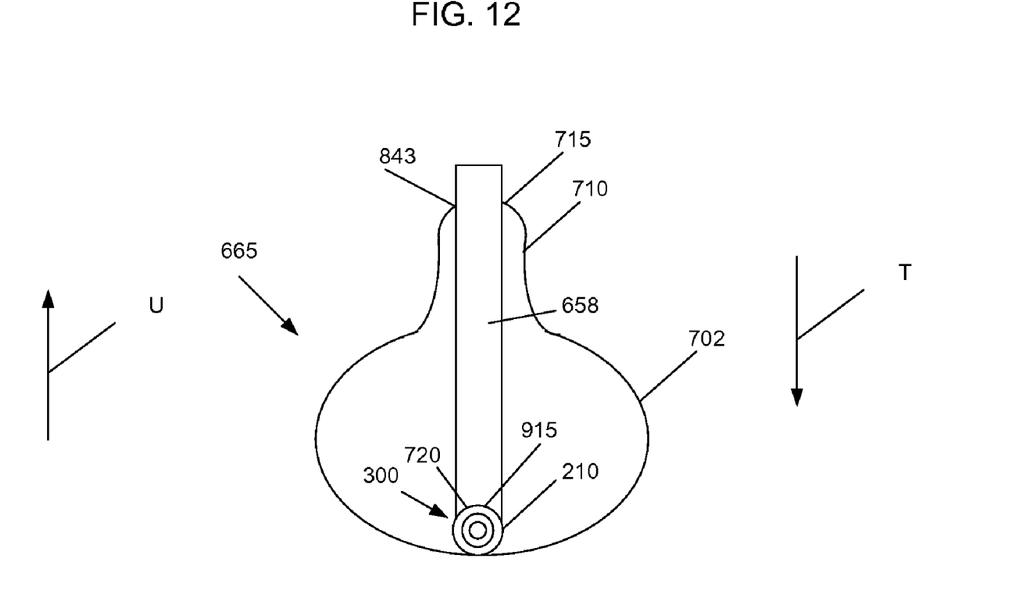
FIG. 12 is a schematic view of a portion of the main cavity of the example molding system of FIG. 11.

For example, referring now to FIG. 12, a schematic view of the cavity 665 formed by the system 800 is shown. The head portion 858 of the actuator member 850 is extended through the aperture 843 into the cavity 665 in a direction T, and an end surface 915 of the head portion 858 contacts the upper surface 720 of the nugget 210.

In example arrangements, the end surface 915 of the head portion 858 is cooled to cool the upper surface 720 of the nugget 210 during molding. The cooling can be controlled to manipulate the wall thickness of the nugget 210 as the nugget 210 is expanded and heated to form the main inflation portion 444 and the bulge 446 of the inflatable member 400. For example, cooling of the upper surface 720 of the nugget 210 can reduce expansion of the nugget 210 during molding to thereby increase wall thickness in the cooled area.

Figure 13:
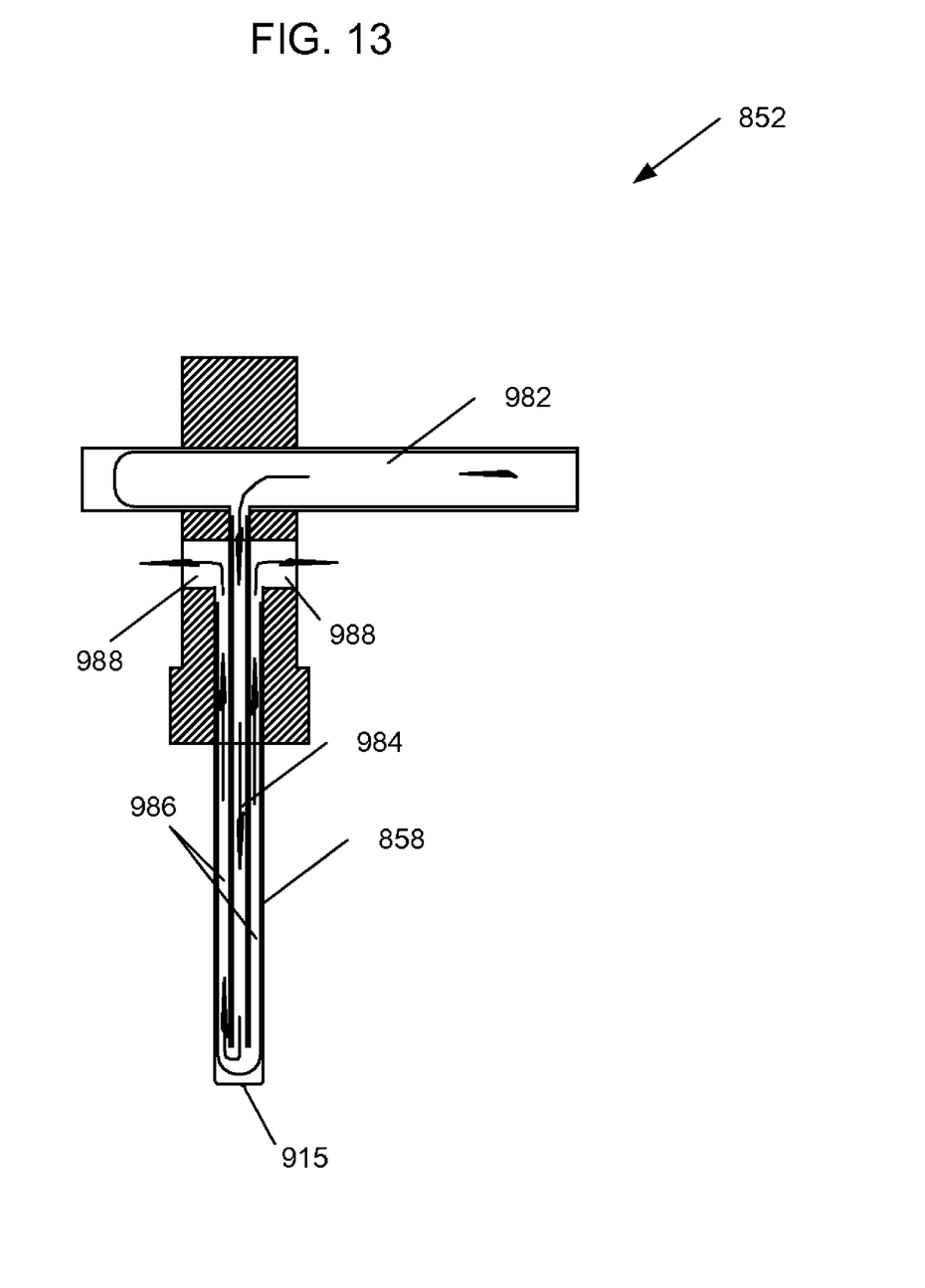
FIG. 13 is a cross-sectional schematic view of a portion of an actuation member of the molding system of FIG. 11.

Referring now to FIG. 13, the pin member 852 is shown in cross-section. The pin member 852 includes an inlet channel 982 through which cooling fluid (liquid or gas) is introduced. The inlet channel 982 is connected to a channel 984 extending through the head portion 984. The channel 984 extends to the end surface 915. Outlet channels 986 extend from the end surface 915 to outlets 988. The cooling liquid can thereby be delivered to the end surface 915 to cool the end surface 915. The end surface 915 can thereby cool the upper surface 720 of the nugget 210 during molding.

In example embodiments, the head portion 984 is forced in the direction T with a given pressure. In some examples, the pressure is between approximately 5 and 50 psi, more preferably between approximately 10 and 20 psi. As the precursor is inflated, the precursor 300 forces the head portion in a direction U (see FIG. 12) opposite to that of the direction T until the end surface 915 of the head portion is flush with the outer surface 715 of the bulge portion 710 (not shown). As the upper surface 720 of the nugget 210 comes into contact with the outer surface 715 of the bulge portion 710, the upper surface 720 is warmed, allowing the material to expand within the bulge portion 710 to form the bulge 446 of the inflatable member 444. The cooling of the upper surface 720 by the end surface 915 prior to expansion of the upper surface 720 into the bulge portion 710 allows for increased wall thickness of the upper surface 720 after molding.

V. Alternative Arrangements and Materials

In other arrangements, molding systems including both actuator members 650, 850 can be used. For example, in one arrangement, the actuator member 650 is used to lift the precursor, and the actuator member 850 is used to cool an upper surface of the precursor.

Other alternatives are possible. For example, in another arrangement, the actuator members 650, 850 can be used to cool or heat the precursor as desired. For example, in one arrangement, the actuator member 650 can be used to cool the precursor at one molding time interval, and then to heat the precursor at another molding time interval.

In alternative arrangements, the actuator members 650, 850 can be replaced with other structures to move head portions into contact with the precursor. For example, springs, motors (e.g., servo or stepper motors), linear drives, hydraulic drives, and shape memory materials can be used in conjunction with, or in place of, the cylinder of the actuator members 650, 850 to move the head portions into contact with the precursor. Other configurations are possible.

The systems and methods described herein can be used to form inflatable members having different shapes from those disclosed herein. For example, the molding systems disclosed herein can be used to form inflatable members with bulges at positions other than the midportion of the precursor. In other alternatives, multiple bulges can be formed, if desired.

The precursors and inflatable members disclosed herein can be made of any suitable balloon material, including compliant and non-compliant materials and combinations thereof. Some example materials for the precursor 100 disclosed herein include thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is SURLYN®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70 D, 72 D, 2533, 5533, 6333, 7033, or 7233 (available from Elf AtoChem, Philadelphia, Pa.). Other examples include nylons, such as aliphatic nylons, for example, Vestamid L2101 1F, Nylon 11 (Elf Atochem), Nylon 6 (Allied Signal), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of material can be found in U.S. Pat. No. 6,146,356, which is incorporated herein by reference.

A variety of materials can also be used to form mold systems 600, 800. In some examples, the components of the mold systems are made of a metal such as stainless steel or copper as described above, although other materials can be used.

CONCLUSION

As described herein, a catheter inflatable member forming mold can include first and second frames that mate to define a mold cavity, the mold cavity defining a main cavity portion and a bulge cavity portion, the mold cavity being sized to receive an elongated tube member therein. The mold can also include a pin member with a head portion positioned in the mold cavity, the pin member extending into the mold cavity, the head portion of the pin member being moveable in a first direction to contact and move the tube member towards the bulge cavity portion of the mold cavity during molding.

In another arrangement, a catheter inflatable tube member forming mold system can include an elongated tube member including a nugget and two end portions, and first and second frames that mate to define a mold cavity, the mold cavity defining a main cavity portion and a bulge cavity portion, the mold cavity being sized to receive the tube member therein. The system can also include a pin member with a head portion positioned in the mold cavity, the pin member extending into the mold cavity, the head portion of the pin member being moveable in a first direction to contact and move the nugget of the tube member towards the bulge cavity portion of the mold cavity during molding.

In yet another arrangement, a method for forming an inflatable member of a catheter assembly can include: placing a tube member into a mold cavity, the mold cavity defining a main cavity portion and a bulge cavity portion; moving a pin member in a first direction within the mold cavity to contact and move the tube member towards the bulge cavity portion; and heating and expanding the tube member within the mold cavity to form an inflatable member.

It is noted that not all of the features characterized herein need to be incorporated within a given arrangement, for the arrangement to include improvements according to the present disclosure.

What is claimed is:

1. A method for forming an inflatable member of a catheter assembly, the method comprising:
   placing a tube member in an unexpanded configuration into a mold cavity, the mold cavity defining a main cavity portion and a bulge cavity portion, the tube member including a nugget portion having an increased wall thickness relative to other portions of the tube member, the nugget portion being aligned with the bulge cavity portion;
   moving a pin member in a first direction within the mold cavity to contact and move the nugget portion of the unexpanded tube member to a first position toward the bulge cavity portion;
   heating the tube member within the mold cavity when the nugget portion is in the first position; and
   while the tube member is being heated, expanding the tube member with a fluid such that a portion of the nugget portion expands into the bulge cavity portion;
   wherein, as the portion of the nugget portion expands into the bulge cavity portion, the fluid exerts a pressure on the pin member moving the pin member in a second direction opposite the first direction allowing the remainder of the nugget portion to expand and fill the main cavity portion.

2. The method of claim 1 wherein the pin member contacts a surface of the tube member opposite of the bulge cavity portion.

3. The method of claim 2 further comprising heating the pin member to provide additional heat to the tube member on a side opposite the bulge cavity portion.

4. The method of claim 1, wherein the tube member is non-uniformly heated.

5. The method of claim 1, wherein the portion of the tube member opposite the bulge cavity portion is heated less than other portions of the tube member.

6. A method for forming an inflatable member of a catheter assembly, the method comprising:
   placing a tube member in an unexpanded configuration into a mold cavity, the mold cavity defining a main cavity portion and a bulge cavity portion, the tube member including a nugget portion having an increased wall thickness relative to other portions of the tube member, the nugget portion being aligned with the bulge cavity portion;
   moving a pin member in a first direction within the mold cavity to contact and move the nugget portion of the unexpanded tube member to a first position away from the bulge cavity portion;
   heating the tube member within the mold cavity when the nugget portion is in the first position;
   while the tube member is being heated, cooling the pin member to cool a surface of the nugget portion facing the bulge cavity portion; and
   expanding the tube member with a fluid when the tube member is being heated and the pin member is cooling the surface of the nugget portion facing the bulge cavity portion such that the surface of the nugget portion facing the bulge cavity portion expands slower than other portions of the nugget portion, wherein, as the tube member is expanding, the fluid exerts a pressure on the pin member moving the pin member in a second direction opposite the first direction.

7. The method of claim 4, wherein the tube member is non-uniformly heated.

8. The method of claim 4, wherein the portion of the tube member adjacent to the bulge cavity portion is heated less than other portions of the tube member.

* * * * *